United States Patent [19]

Kelly et al.

[11] Patent Number: 5,227,033
[45] Date of Patent: Jul. 13, 1993

[54] ELECTROLYTIC ETCHING OF METALS TO REVEAL INTERNAL QUALITY

[75] Inventors: John H. Kelly, Burlington; Leonard E. Guest, Binbrook, both of Canada

[73] Assignee: Stelco Inc., Hamilton, Canada

[21] Appl. No.: 897,085

[22] Filed: Jun. 11, 1992

Related U.S. Application Data

[60] Continuation-in-part of Ser. No. 519,394, May 4, 1990, Pat. No. 5,061,352, which is a division of Ser. No. 745,276, Aug. 14, 1991, Pat. No. 5,186,796.

[30] Foreign Application Priority Data

Jun. 5, 1989 [CA] Canada .................................. 601708

[51] Int. Cl.⁵ ................................................ C25F 3/02
[52] U.S. Cl. .............................. 204/129; 204/129.35; 204/141.5; 204/129.75
[58] Field of Search ................ 204/129, 129.35, 141.5, 204/129.75, 224 M

[56] References Cited

U.S. PATENT DOCUMENTS

| | | | |
|---|---|---|---|
| 2,745,805 | 5/1956 | Jones, Jr. | 204/224 M X |
| 4,533,642 | 8/1985 | Kelly | 436/78 |
| 4,718,992 | 1/1988 | Funahashi et al. | 436/78 |
| 5,028,304 | 7/1991 | Stanishevsky et al. | 204/129.75 |
| 5,062,931 | 11/1991 | Kephart | 204/129.7 X |

Primary Examiner—Donald R. Valentine
Attorney, Agent, or Firm—Sim and McBurney

[57] ABSTRACT

The internal quality of continuously cast and other steel samples in the form of ingots, billets, blooms, slabs and bars is determined in rapid manner to enable potentially problem-causing casting conditions to be identified and corrected in timely manner. A steel sample from the casting, after grinding to remove any heat-affected zone and to provide a desired degree of surface roughness, is anodically etched using dilute hydrochloric acid at ambient temperature to etch away metal from the surface to reveal the internal quality. After removal of the sample from the etching apparatus, the sample is washed, dried, and visually examined to determine the internal quality.

24 Claims, 6 Drawing Sheets

ELECTROLYTIC ETCHING OF METALS TO REVEAL INTERNAL QUALITY

REFERENCE TO RELATED APPLICATION

This application is a continuation-in-part of copending U.S. patent application Ser. No. 519,394 filed May 4, 1990, now U.S. Pat. No. 5,061,352, which is a division of application Ser. No. 745,276, filed Aug. 14, 1991, now U.S. Pat. No. 5,186,796.

FIELD OF INVENTION

The present invention relates to an electrolytic procedure for the etching of metal pieces, particularly continuously-cast metal pieces, to reveal the internal quality of the metal piece.

BACKGROUND TO THE INVENTION

In the continuous casting of steel products, which may be in the form of a billet, bloom or slab, molten steel is delivered to the upper end of a vertical casting mold of the dimensions desired for the product. As the steel descends in the mold, it commences to solidify from the exterior towards the interior. While still in a pliable state, the solidifying steel is guided through a curved path to a horizontal direction.

The operating characteristics of the continuous casting procedure need to be known and under close control to maintain safe, efficient continuous casting. Process control is verified by evaluating the internal quality in at least the cross-section and at other times the longitudinal section of the cast steel. Steel is considered to have satisfactory internal structure if there are no internal cracks, no internal voids, no internal porosity, no inclusions and internal symmetry of zones of solidification.

Immediately after the product is solid, a sample can be cut from the cross-section and, after surface preparation, the sample is tested by either or each of two conventional methods, namely sulphur printing or acid etching. If the sulfur content of the steel is less than 0.010% S or deoxidized with aluminum, only the acid etching method is workable.

Conventional acid etching procedures are time consuming and unreliable in providing a rapid processing of a steel sample to reveal its internal quality. Such acid etching (ASTM Standard E381-79) generally involves selective attack on the metal surface by an aqueous acid solution comprising 1 to 1 v/v technical grade hydrochloric acid at about 70° to 80° C. for longer than about 20 minutes, the time depending on the initial temperature of the metal, followed by visual inspection of the etched surface.

Electrochemical etching and electropolishing of small metal specimens is part of the existing art of chemical analysis and metallography. For example, U.S. Pat. No. 4,533,642, assigned to the assignee hereof, describes an electrolytic etching procedure for determining the acid-soluble aluminum content of small steel samples. This procedure employs small quantities of steel to determine the specific content of aluminum by chemical analysis of the spent etchant. The electrolytic etching of large scale metal samples does not appear to have been practiced previously and not for the purpose of determining the internal quality of a steel sample, as is effected herein.

One of us, John H. Kelly, is aware, by private communication, the Inco Ltd, in the UK, has utilized an electrolytic etching process on nickel and nickel alloys to determine the internal quality of samples of the metal. Details of the process are trade secret but such information as is known to me indicates a process using stronger acid and a lower current density than is employed herein. These parameters suggest to me that the application of current is secondary tot he process and etching is effected mainly by chemical reaction with the acid. In contrast, the etching procedure described herein is truly coulometric, requiring current flow to effect etching, since the etchant itself is unable significantly to react with the sample surface in the absence of such current.

SUMMARY OF INVENTION

In accordance with the present invention, there is provided a novel method of etching metal (including an alloy of two or more metals) pieces to reveal their internal quality by using electrolytic procedures, which provides a rapid, readily-controlled, safe and environmentally-acceptable operation at ambient temperatures.

Accordingly, in one aspect of the present invention, there is provided a method of determining the internal quality of a mass of metal, such as an ingot, slab, bloom, billet, bar, forging, casting and/or welded fabrication of an etchable metal, such as iron, plain carbon and low alloy steel, tool steel and stainless steel, nickel and chromium, or an alloy of two or more of such metals, which comprises a plurality of sequential operations.

A sample first is removed from the mass of metal by any convenient procedure and the surface to be examined is cold machined, such as by milling, to remove any heat-affected zone and preferably to provide a surface having a peak-to-valley surface roughness ($R_Z$) of less than about 6.8 $\mu$m. The machined surface then is electrolytically etched using an aqueous etchant for the metal, usually an aqueous acid etchant to remove at least about 0.5 mil (about 12 $\mu$m) of steel from the surface of the sample so as to expose a surface representative of the internal quality of the steel mass from which the sample was taken. The etched surface of the sample then is treated to remove aqueous etchant and any deposit therefrom and then dried. The dried etchant surface then is visually examined for its internal quality.

GENERAL DESCRIPTION OF INVENTION

Figure 1:
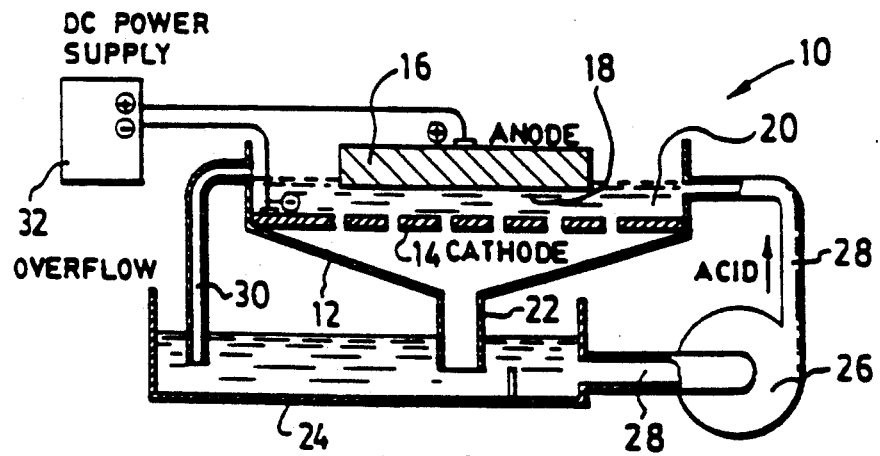
FIG. 1 is a schematic illustration of one form of electrolytic etching apparatus useful in the present invention for the treatment of billets and small samples wherein stationary electrodes are employed.

The present invention is broadly applicable to the determination of the internal quality of metal at a particular plane within a mass of metal. The determination may be made for either the transverse or longitudinal plane of continuously cast or ingot cast metals or of hot-or cold-rolled metals. The invention is particularly described hereafter with respect to steel. However, the invention is applicable to other etchable metals, including iron, nickel and chromium, as well as alloys of such metals.

Samples for treatment and examination by the method of the invention may be cut from the transverse or longitudinal planes of ingots, blooms, slabs, billets, bars, forgings, casting or welded fabrications. However, ingots usually are rarely studied and then only at the time of introducing a new mold design or a new grade of steel. Continuously-cast blooms, slabs and billets usually are routinely tested and hot-rolled blooms, slabs and billets sometimes may be tested. All such test operations when desired to be carried out may be effected by the method of the present invention.

The procedure of the present invention particularly involves analysis of steel slabs, blooms and billets formed by the continuous casting of steel for the internal quality of the steel. A sample for testing is removed from the steel in any convenient manner and is milled to a depth which removes any heat-affected zone in the surface of the metal and provides a surface preferably having peak-to-valley roughness of less than about 6.8 $\mu$m, so that the features revealed by the acid etching are not obscured by tool marks. Such heat-affected zone initially may be absent from the sample, depending on the procedure employed to form the sample, and the sample may have the desired surface roughness in which case the milling step may be omitted. For both transverse and longitudinal sections, a slice is required of suitable thickness, as dictated by the cutting, milling and grinding methods. The final thickness can range from approximately 1½ to 2 inches with the extreme limits ranging from about ¼ to 3 inches. Thinner samples than ¼ inch can be joined to thicker material and then etched, if necessary. In the case of bloom and slab samples, the slice is further subdivided into manageable lengths and widths, ranging from about 8×8 to about 13×24 inches.

Steel then is electrolytically etched from the milled surface using an aqueous etchant to reveal the internal quality. For steel, an aqueous acid etchant is preferred. However, for other metals, an alkaline electrolyte may be employed.

It is essential in the present invention to remove at least about 0.5 mil (i.e., at least one half of one-thousandths of an inch or about 12 $\mu$m) and generally up to about 6 mils (about 150 $\mu$m) of steel from the milled sample in order satisfactorily to reveal the internal quality of the steel sample. It is noted that this quantity of metal removed contrasts markedly with that involved in etching small steel samples to determine the aluminum content thereof, where only a small amount of steel needs to be dissolved to make the analytical determination of aluminum content of the steel sample and, in fact, the removal of large quantities of metal seriously impairs the analytical process. In the process of the invention, a significant depth of metal must be removed from the milled surface of the sample to expose the internal quality of the sample.

The steel sample is the anode during the etching and is positioned adjacent to and closely spaced from a suitable cathode while an electric current is passed between the two through a suitable aqueous acid etchant as electrolyte.

Anodic electrolytic etching produces hydrogen bubbles at the cathode. The hydrogen bubbles displace the electrolyte and cause non-uniformity of current density and hence a non-uniform rate of removal of metal from the anode. In addition, if still acid is used, the electrolyte becomes depleted of acid at the metal surface and insoluble hydrated metal oxide forms, which tends to inhibit further metal removal.

Accordingly, in the present invention, the anodic dissolution is effected in such manner as to displace the hydrogen bubbles from the current path and to rapidly move the reaction products away from the metal surface. Generally, this is achieved by circulating electrolyte through the space between the anode and cathode at any convenient recirculation rate, generally about 10 to about 60 L/min of acid etchant, to achieve a flushing action.

The gap between the anode and cathode to some extent controls the velocity of the etchant across the sample surface, since, at a constant etchant recirculation rate, the resulting velocity of etchant increases as the gap decreases and decreases as the gap increases. Generally, the gap between the anode and cathode varies from about 0.2 to about 0.4 inch (i.e. about 0.5 to about 1 cm), preferably about 0.25 to about 0.30 (i.e. about 0.65 to about 0.76 cm).

The recirculation rate of acid etchant referred to above, taking into consideration sample width and gap between sample and cathode, is about 1.6 to about 3.2 L/min/cm of sample width/cm of gap between sample and cathode.

With smaller metal samples, for example, a 4"×4" billet slice, it is convenient to provide the anode and cathode stationary with respect to one another during the electrolysis. In this arrangement, it is preferred to employ a perforated plate cathode to facilitate circulation of electrolyte through the gap between the anode and cathode to achieve the desired flushing action to remove gaseous hydrogen and reaction products. This arrangement is not satisfactory for larger metal samples, for example, 8"×13" for a bloom slice or 9¼"×12" for a slab slice, since hydrogen tends to hang up under the center of the sample. The perforated cathode may be located below or above the anodic sample in a bath of electrolyte. Provision is made for recirculation of electrolyte between the bath and the gap between anode and cathode.

With larger metal samples, such as those taken from blooms and slabs, it is advantageous to provide relative linear motion between the anodic sample and the cathode while the anode and cathode remain spaced the same distance apart. This operation also may be employed with ingot, billet and rod slices, if desired. In this arrangement, the cathode preferably is in the form of an elongate tubular rod having a slit extending the length thereof to facilitate circulation of electrolyte through the gap between the anode and cathode to achieve the desired flushing action. In addition, the combination of an elongate circular bar cathode and relative linear movement of anode and cathode permits a much higher local current density to be applied to a portion of the surface of the anodic sample for the same average current density, so that dissolution of metal can be effected uniformly.

The tubular cathode may be moved above a stationary anodic sample immersed in electrolyte, or the anodic sample may be moved above the tubular cathode, which is maintained stationary. Provision in either case is made for recirculation of electrolyte between the electrolyte bath and the interior of the tubular cathode. The relative motion between anode and cathode is such that the whole surface of the anodic sample is traversed at a constant speed, so that a uniform quantity of steel is etched from the surface. The electrochemical conditions and speed of relative movement may be such as to complete the desired dissolution in one pass, or in a single reciprocal pass or in multiple passes.

Alternatively, an insulating plate having an elongate slot formed therein may be positioned between a plate-like cathode and the stationary anode sample. Movement of the insulating plate relative to the stationary anode and cathode then permits current to flow through the slot with a high local current density to achieve uniform etching of the anodic surface, in the same way that movement of the tubular cathode relative to the stationary anode produces uniform etching.

The electrolytic etching is effected to remove steel from the anode surface in an amount sufficient to expose a representative internal quality. As noted above, a minimum of about 0.5 mil of steel is required to be removed from the sample. Once the internal quality has been exposed by anodic dissolution, further etching does not reveal any new information. Generally, about 1 to about 5 mils (about 25 to about 125 μm) of steel are removed during the etching step.

The electrolytic conditions required to effect the desired degree of etching depend to some extent upon the etchant employed, the procedure employed to effect the etching and the size of the sample employed. Generally, the electrolytic etching is carried out suing a current of about 100 to about 600 amps applied at an effective currently density of about 4 to about 24 amp/cm². For steel, it has been determined that the thickness of metal etched from the sample is given by the relationship:

$$t = 0.136 \times J/S$$

where t is the thickness of metal removed, J is the amperes per inch width of sample and S is the scan rate in inches per minute. The preferred current per inch of sample width is about 33 to about 50 amperes. For determining whether segregation has occurred in the sample, a current per inch of sample width of about 10 to about 25 may be applied, in a separate etching from that determining internal structure. A compromise of the current density ranges may permit both material quality and segregation to be determined in a single etching operation.

When etching with stationary anode and cathode, the effective current density is current divided by the total surface area of the sample surface being etched. However, when etching with relative movement of anode and cathode, the effective current density is current divided by the area of the sample being etched adjacent the cathode only.

The electrolytic etching generally is effected using dilute hydrochloric acid, usually having an acid normality of about 0.1 to about 3.0 N, preferably about 0.2 to about 2.0 N, or a concentration of about 10 to about 30% v/v Hcl, at net ambient temperatures, usually from about 10° to about 40° C., preferably about 20° to about 40° C. The desired degree of etching generally is complete in about 40 to about 400 seconds, depending on the size of the sample.

Other convenient dilute aqueous etchants which are activated by electric current may be used, if desired. Other etchants which may be used include dilute chromic acid, a dilute mixture of nitric and hydrochloric acid, dilute sodium hydroxide and dilute sulfuric acid.

The electrolytic etching of the steel to remove metal from the surface desired to be inspected tends to cause a black gelatinous coating or precipitate to form over the steel surface. This coating, however, is readily removed in subsequent process.

After the etched sample is removed from the etching apparatus, the sample is rinsed with water, rubbed vigorously with cleansing powder to remove the coating, if present, from the etched surface, followed by rinsing and drying with an air gun.

Alternatively, following cleaning of the etched surface by brushing and rinsing, cathodic cleaning of the surface may be employed for final clean-up of the prepared surface. Such cathodic cleaning may be effected by reversing the polarity of the sample from positive to negative in the presence of an electrolyte, so as to generate just sufficient hydrogen at the sample surface to lift off any loosely adhering soil left by the etching process, but insufficient to dislodge slag and occlusions. The brushing step tends to smear the black gelatinous coating left by the etching process and the cathodic cleaning removes the smear.

A clear acrylic resin coating may be applied tot he etched surface to protect it against oxidation. The sample then can be studied visually for the internal quality condition of the sample.

In addition, rather than rinsing the etched surface completely, an alkaline rinse first may be effected to neutralize trapped acid sites in hairline cracks and small holes in the etched surface, so that darkly colored hydrated iron oxide forms and is more readily seen visually, thereby facilitating identification of the internal quality.

Some steels contain relatively high levels of copper, for example, 0.30 wt. % instead of a more normal approximately 0.03 wt. % Cu. When electrolytic action is effected on a sample of such steel in accordance with the present invention, copper also goes into solution and some of the copper may become deposited on the cathode. When the current is turned off, the cathode preferably is moved away from the etched sample far enough so that deposited copper is not transferred from the cathode to the nearest portion of the etched sample. A sacrificial steel bar may be placed adjacent the cathode to avoid the sample becoming contaminated by copper.

The same electrolyte bath is employed for a number of successive etchings. During such successive anodic etchings, there is a build up of solubilized iron in the bath of electrolyte and a depletion of the effectiveness of the acid. The electrolyte requires replacement from time to time as it becomes depleted in this way. The replacement should be made before a noticeable increase occurs in the formation of hydrated iron oxide, otherwise insolubilized hydrated iron oxide may form along with copper staining of the sample surface.

The decision as to when to replace the depleted electrolyte may be based on any convenient basis, for example, a measurement of the total time for which the electrolyte has been employed. Alternatively, where the cell geometry is constant, the cell voltage may be measured and depleted electrolyte may be replaced when the cell voltage has increased to a predetermined level, for example, a voltage of 12 volts increasing to 24 volts.

Since the internal quality of the sample can be rapidly determined by the present invention, any irregularities that examination of the internal quality reveals can be communicated to the operating staff for any adjustment required to the operating conditions for the particular steel-making operation in respect of which the test has been carried out, for example, the operator of a continuous caster.

In comparison to the conventional hot acid etching procedure for exposing internal quality, the present invention exhibits certain advantages. Since a cold dilute hydrochloric acid is employed in the present invention, fume formation at elevated temperatures and the safety hazard of hot strong hydrochloric acid associated with the prior art procedure are avoided. Further, since hydrogen is generated only at a desired surface, namely the cathode, and not from the sample itself, as opposed to the prior art where hydrogen is generated from the whole sample, there is less potential for the formation of explosive gas mixtures.

In addition, the speed of reaction of the electrolytic process employed herein is dependent mainly on current density whereas with the prior art hot acid etch process is very much dependent on other factors, including sample temperature, acid temperature, acid concentration, sample position in tank and metal grade.

Further the electrolytic etching of the steel sample herein tends to reveal slag and inclusions as they exist in the sample, whereas the hot acid etch method tends to dissolve and/or dislodge. When dissolved and/or dislodged, the slag and inclusions leave behind voids which are not clearly distinguishable from the true voids left by argon bubbles and the like. The hot acid etch process, therefore, is much less reliable than the process of the invention in revealing the true nature of the internal quality of the steel samples.

DESCRIPTION OF PREFERRED EMBODIMENT

Referring to the drawings, FIG. 1 illustrates one form of etching apparatus 10 having an etching vessel 12 which has a fixed perforated cathode 14 extending across the base of the vessel and an anode 16 comprising the sample to be etched spaced apart a short distance from the cathode to define a gap 18 therebetween.

A bath 20 of dilute hydrochloric acid is located in the vessel 12. The etching vessel 12 communicates at its lower end with a pipe 22 which permits dilute hydrochloric acid in the bath 20 to flow into a lower etchant reservoir vessel 24. A recirculation pump 26 communicates through pipes 28 with the etchant reservoir 24 and the etching vessel 12 to recirculate the acid from the reservoir 24 to the vessel 12.

The vessel 12 is provided with an overflow pipe 30 to maintain a constant level of acid in the vessel 12 during the etching operation.

In operation, the acid is circulated between the reservoir 24 and the vessel 12 by the recirculation pump 26 to provide a level of acid below the overflow level. The sample 16 then is positioned in the vessel 12 so that the surface to be etched is below the acid level and is spaced from the cathode 14 by the gap 18.

An electric current then is applied from a power source 32 between the cathode and anode while the acid bath is circulated. Metal is etched from the anode sample 16 and hydrogen is formed at the cathode. The circulation rate of the acid is such as to flush the hydrogen out of the gap 18 so as to prevent gas building at the anode and permit uniform etching. The flushed-out hydrogen is vented from the vessel 12. The perforated form of the cathode 14 permits the electrolyte to circulate.

When the desired degree of etching has been effected, the current is turned off, circulation of the acid ceased and the metal sample 16 removed. The apparatus of FIG. 1 is suitable only for billet samples of about 4 to 6 inches square, since hydrogen tends to accumulate near the center of the section with large-sized samples.

Figure 2:
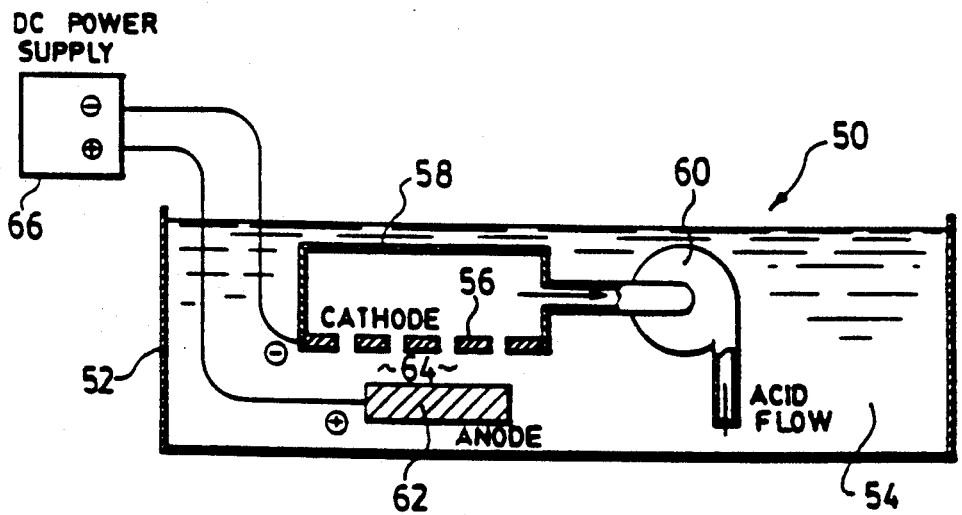
FIG. 2 is a schematic illustration of an alternative form of electrolytic etching apparatus to that illustrated in FIG. 1.

The arrangement of FIG. 2 is an alternative to that of FIG. 1. As seen therein, the apparatus 50 comprises a single tank 452 containing a bath 54 of acid etchant. A perforated cathode 56 communicates with a submerged vessel 58 which, in turn, communicates with a recirculation pump 60 for the recirculation of etchant from the bath 54.

A steel sample 62 is positioned immersed in the bath 54 below and spaced from the cathode 56 by a gap 64. Electrical current is applied between the anodic sample 62 and the cathode 56 by a suitable power source 66, while the electrolyte is circulated.

The apparatus of FIG. 2 is inconvenient except for smaller samples but may be employed with such samples to effect rapid etching of the surface to be inspected.

In the embodiments of FIGS. 1 and 2, the sample is maintained in a fixed position relative to the cathode during etching and the whole of the surface of sample is in contact with the circulating bath. It is preferred, however, to employ relative movement between anode and cathode and exposure of part only of the sample to circulating electrolyte at any given time. The latter arrangement enables much higher instantaneous current densities to be employed and hence rapid metal removal to be effected. With larger bloom and slab samples, this arrangement avoids the hydrogen accumulation problem mentioned above.

Figure 3:
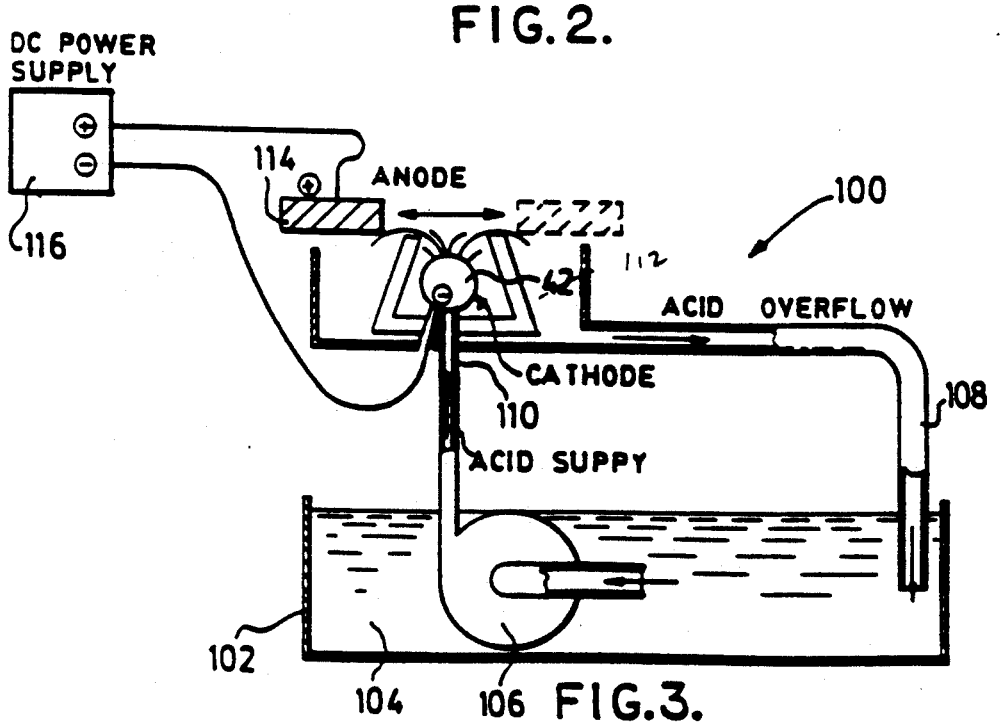
FIG. 3 is a schematic illustration of one form of electrolytic etching apparatus for bloom and slab samples wherein the anode moves relative to the cathode.
Figure 4:
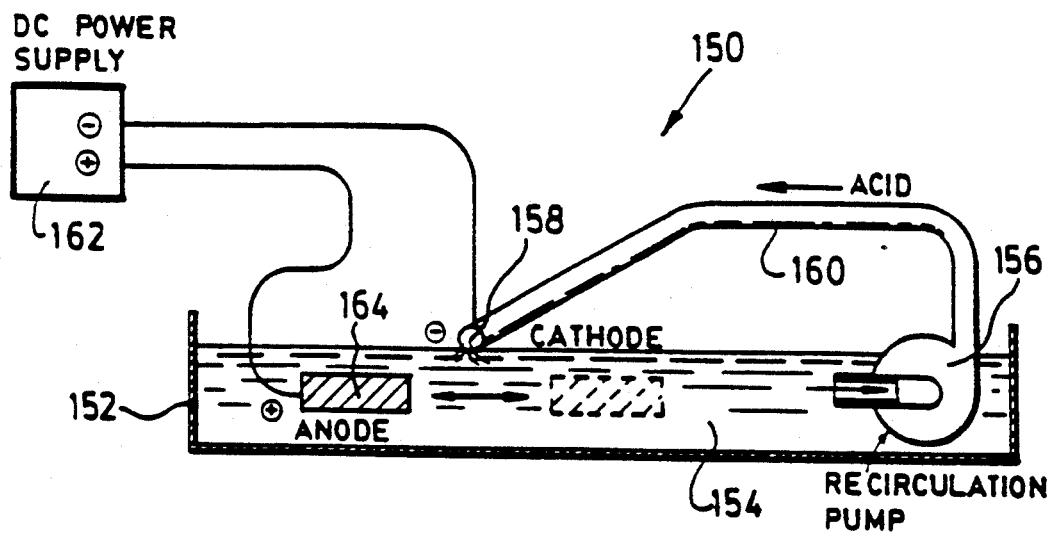
FIG. 4 is a schematic illustration of an alternative form of electrolytic etching apparatus for bloom and slab samples to that illustrated in FIG. 3.

One embodiment of such apparatus useful for bloom and slab samples, but which also may be used for billet samples, is shown in FIG. 3 while another embodiment of such apparatus is also useful for bloom and slab slices, which are more conveniently handled by total immersion in acid, is shown in FIG. 4.

In FIG. 3, the etching apparatus 100 comprises a reservoir tank 102 in which a reservoir 104 of etchant acid is housed. A recirculating pump 106 communicates with the etchant reservoir 104 as does a return acid overflow pipe 108.

The recirculating pump 106 communicates by pipe 110 with a slotted nozzle 112 which is in the form of an elongate tube and acts as a cathode and from which acid etchant flows to form a fountain of defined weight, sufficient to react the anodic sample. A sample 114 to be etched is gripped by a suitable mechanism, which also may be employed to make the electrical connection thereto for movement relative to the cathode 112.

An electrical power source 116 applies an electric current between the anode and cathode while the anodic sample 114 is moved linearly relative to the cathode 112, and in contact with the fountain of acid etchant formed by the cathode 114 in the portion of the sample 114 adjacent to the fountain. In this way, etching occurs only at a small area of the sample at any given time as electrolyte sweeps across the anodic surface of the sample at high speed. The spacing between the anodic sample 114 and the cathode 112 is maintained constant during the relative movement to ensure uniform etching. The etching may be effected in a single pass or in a reciprocal pass (i.e., etching occurs on both a forward and a reverse pass). Spent etchant returns to the reservoir 104 via the overflow pipe 108. Since only a small area of the sample 114 is exposed to electrolyte at one time, much higher instantaneous current densities are possible.

The etching procedure for the FIG. 3 embodiment may be automated for heavy slab or bloom slices as described below with respect to FIGS. 7 and 8.

Although the anode sample 114 is shown moving relative to the stationary cathode 112 in FIG. 3, obviously the same effect can be obtained by moving the cathode 112 relative to a stationary anode 114.

In FIG. 4, the apparatus 150 comprises a tank 152 containing an acid etchant bath 154 having a recirculation pump 156 communicating between the bath 154 and an elongate slotted nozzle 158 through pipe 160. The slotted nozzle 158 is connected to a power supply 162 as the cathode.

A sample 164 is connected to the power supply 162 to be the anode and is moved relative to the slotted nozzle 158, or, alternatively, the slotted nozzle 158 may be moved relative to the sample 164. In addition, etching may be completed in embodiment of FIG. 3, the spacing is maintained constant during the relative movement of spray head 158 and sample 164. In addition, etching may be completed in a single pass or in a reciprocal pass.

The etching procedure for the FIG. 4 embodiment may be automated for heavy slab or bloom slices to effect the following mechanical motions, namely manually placing the slice facing upwards on an elevator support, lowering the slice into the tank, filling the tank with electrolyte, slowly moving the cathode tube or the slice while the power is on, during which time the electrolyte is rapidly pumped across the sample face, either through openings in the tube-like cathode or from an adjacent array of nozzles, to effect the desired degree of etching and raising the sample from the tank after the current has been turned off.

Figure 5:
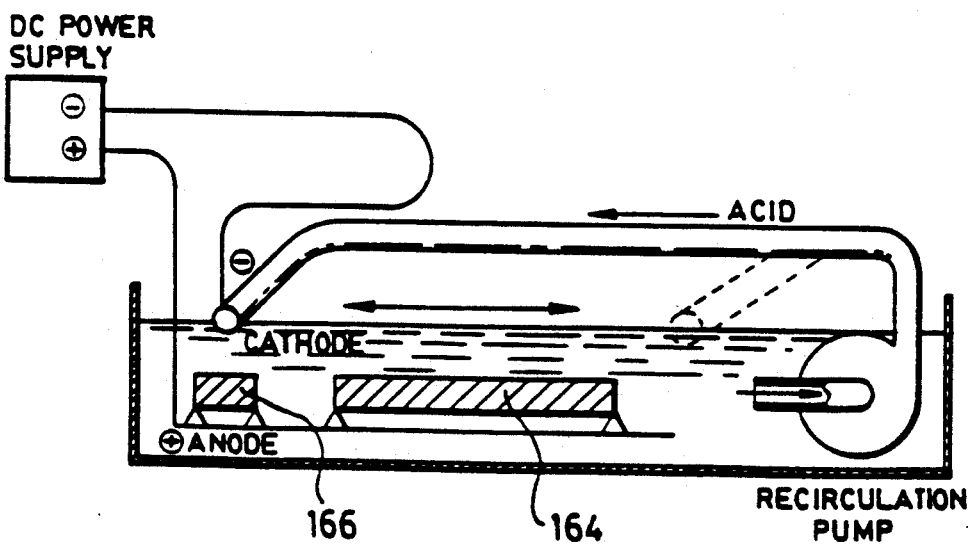
FIG. 5 is a schematic representation of a further alternative form of electrolytic etching apparatus for bloom and slab samples using a sacrificial steel bar for high copper steels.

FIG. 5 is similar to FIG. 4, except that it employs a sacrificial steel bar 166, to prevent deposition of copper on the steel sample 164 when etching high copper content steels, such as may occur when the current is turned off, such copper instead being deposited on the steel bar 166.

Figure 6A:
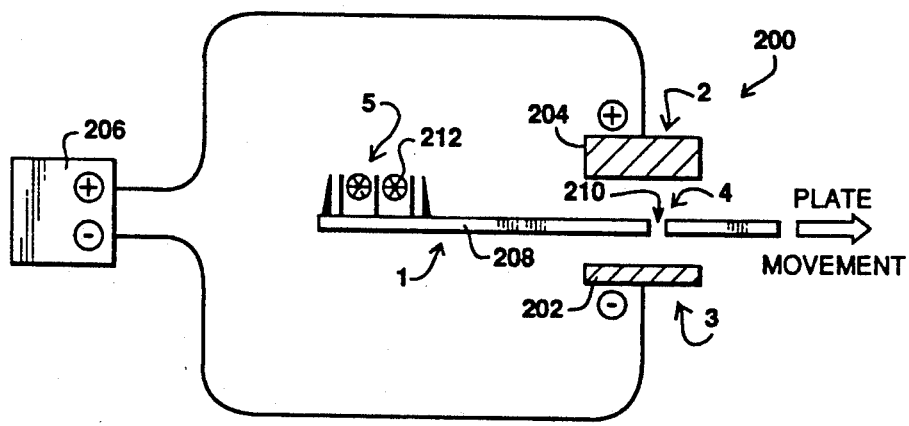
FIG. 6 is a schematic representation of an additional alternative form of electrolytic etching apparatus useful in the present invention.
Figure 6B:
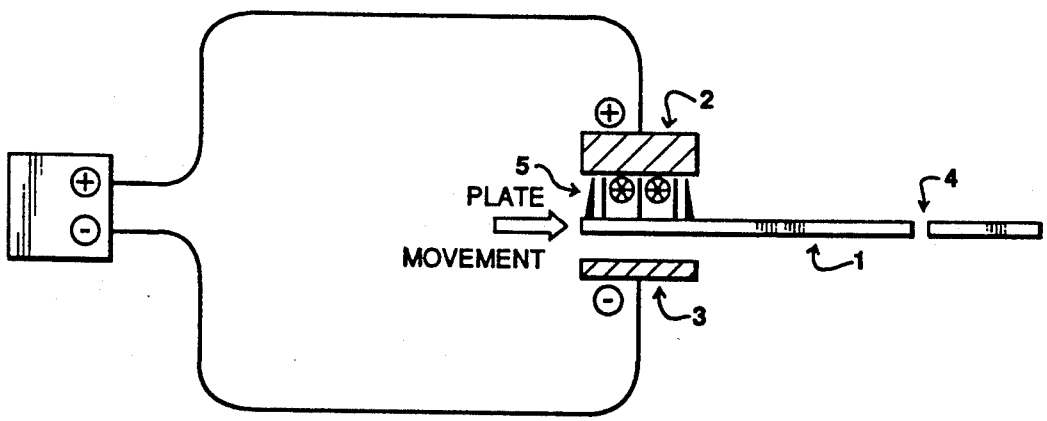

Referring to FIG. 6, this structure achieves the same type of effect as in FIGS. 3 and 4, with uniform etching being effected with a high local current density. In this embodiment, etcher 200 employs a stationary plate-like cathode 202 and a sample anode 204 to which current is applied by a power supply 206. Located between the anode 204 and cathode 202 is a plate 208 of insulating material having an elongate slot 210 formed therein.

The slot 210 constrains the current flow between anode and cathode. As the plate 208 is moved relative to the electrodes, etching occurs only in the portion of the anode 204 aligned with the slot 210. Etching may be effected in a single one-way pass, a reciprocal pass or multiple passes. By maintaining a uniform speed of movement of the plate 208, a uniform etching of the sample is effected.

Provision is made for recirculating acid over the electrode faces (not shown) to remove gas and etched material from the electrode surfaces.

The moving plate 208 may be equipped with sprayers 212 to permit brushing, rinsing, neutralizing and drying of the sample 204 when in the position 6B in FIG. 6.

Following the dissolution of the metal from the desired surface in the apparatus of any one of FIGS. 1 to 5, the metal sample is removed from the electrolytic apparatus, washed, scrubbed, dried and then visually inspected for internal quality.

Figure 7:
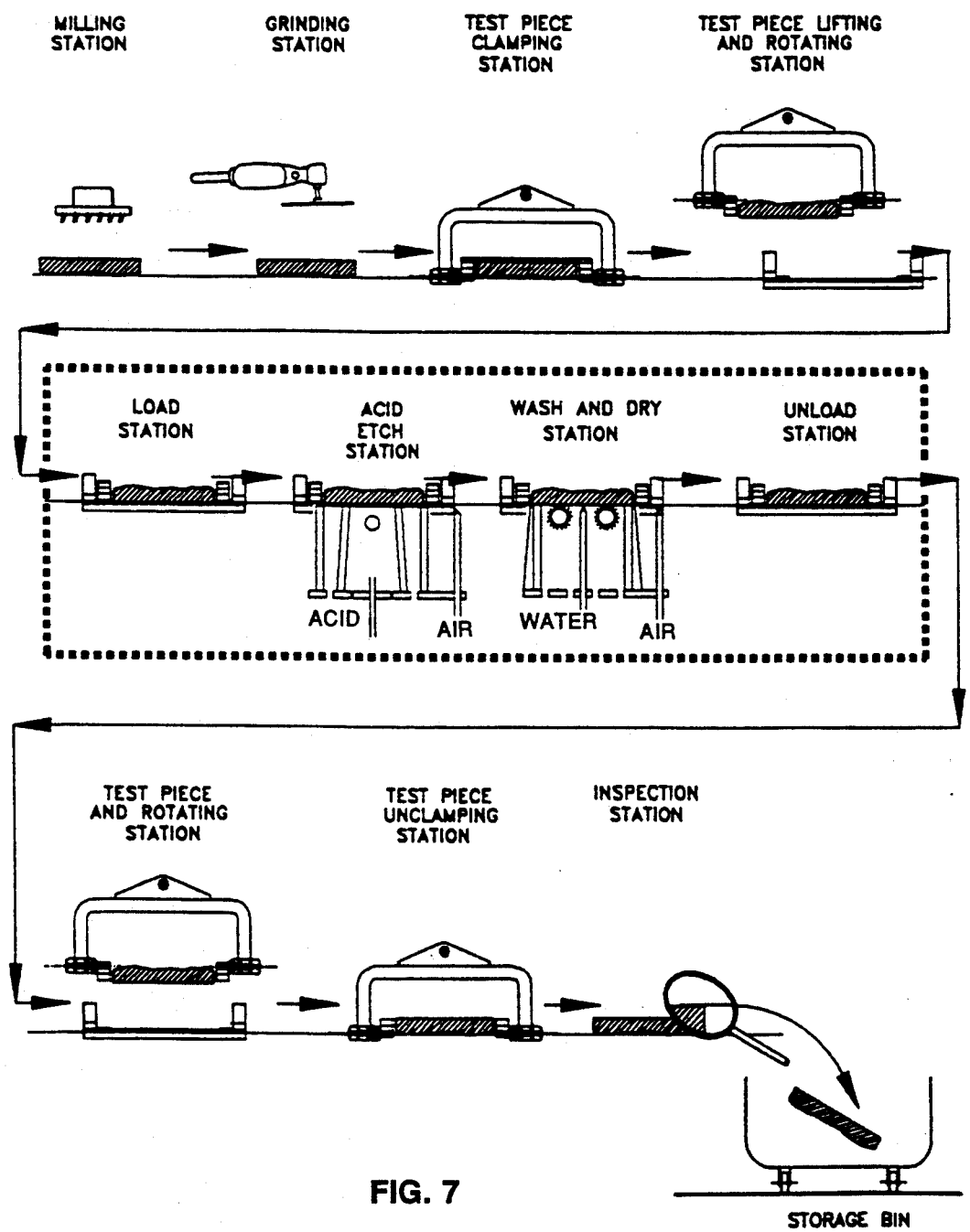
FIG. 7 is a schematic flow diagram for an automated procedure for heavy slab or bloom slices.
Figure 8:
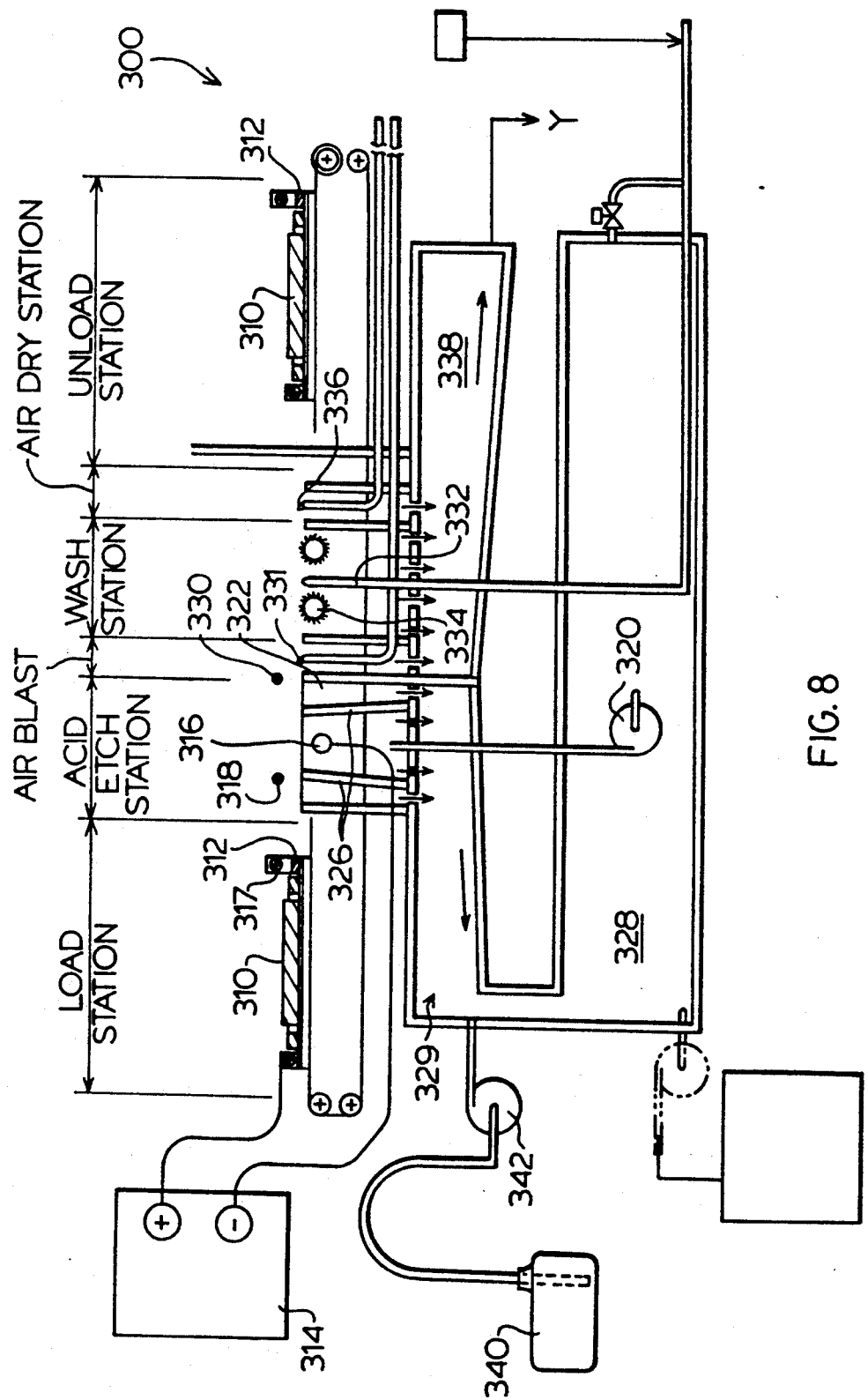
FIG. 8 is a detail diagram illustrating the etching stage of the overall procedure of FIG. 7.

Referring to FIGS. 7 and 8, there is illustrated therein an automated test procedure in accordance with one preferred embodiment of the invention. As seen in FIG. 7, a sample passes through a plurality of stations, involving an initial upper surface preparation by initial milling and subsequent grinding. The sample then is clamped in a transfer device which rotates the sample so that the prepared surface faces downwardly.

The sample then is transferred to the loading station of an etching device 300 shown in more detail in FIG. 8. At the loading station, the sample 310 is mounted into the sample carrier 312 of suitable construction to transport the sample 310 horizontally through the etching device 300. Any suitable device mechanism may be employed for transporting the sample on the carrier 312 through the etching device. A power supply 314 is connected one pole to the sample carrier 312 and hence the sample 310 and the other pole to a rod-like cathode 315 extending transversely across the etching device 300. The power supply is switched on just before the sample 310 encounters etchant with the sample terminated. However, power could be applied continuously tot he sample and the cathode, if desired, since current will flow only when the sample is in contact with the etchant.

The sample 310 is transported by the carrier 312 until a sensor 317 mounted on the carrier encounters a first position target 318, which activates the flow of etchant acid by pump 320 to chamber 322 in which also is positioned the rod-like cathode 316. Upon the sample 310 coming into contact with the acid etchant passing over its surface, etching of metal from the anodic sample occurs until all the lower surface of the metal has been exposed, whereupon etchant liquid flow ceases. The depth of etching which is achieved is coulometric, so that the depth of etching depends only on the ratio f the current per unit of width tot he uniform speed of relative motion, and expressed in units of amperes per inch of sample width. The electrolyte macroetch is independent of the parameters of acid strength and temperature within its operable ranges of about 10° to about 40° C. and about 0.1 to about 0.3 N.

The continuous flow of acid etchant during etching by circulation by pump 320 ensures that hydrogen gas does not accumulate at the surface being etched, but rather is swept away by the flowing etchant which overflows weirs 326 for return to an acid reservoir 328 in which the recirculating pump 320 is immersed via an acid return sump 329.

While etching of the sample 310 continues, the forward portion of the sample carrier begins to leave the acid etch station. The sensor 317 encounters a second target 330 which activates a first air knife 331, which directs an air blast angularly against the etched surface to blow acid etchant backwards across the surface. The target 330 also activates a second air knife 336 is located at the downstream end of the wash station to blow excess cleaning solution backwards across the surface of the sample, so that the sample leaves the wash station in an almost dry condition.

Spent cleaning solution from the wash station is collected in a sump 338 and discharged to drain. Fresh acid is fed to the acid reservoir 328 from a reservoir 340 by a pump 342. The level of the solution in the etch station and the wash station are maintained by an automatic replenishment arrangement.

When the rear end of the carrier 312 passes from the wash station, the cleaning solution flow to nozzle 332, the brushes 334 and the air knives 330 and 336 are turned off. The carrier 312 continues to transport the sample 310 to an unloading station.

The sample 310 is unloaded by suitable unloading means, rotated and transported to an inspection station where the sample is unloaded, so that the etched surface of the sample can be inspected to determine the internal quality of the mass of metal from which the sample was taken.

The sample carrier 312 is retracted by the drive mechanism within the etching drive 300 to the load station, ready to receive the next sample for transportation through the device. Alternatively, a new sample may be loaded at the unloading station and transported by the carrier to the loading station. Similarly, the etched sample may be transported on the carrier back to the loading station for unloading at that location.

Modifications may be made to the illustrated structures. For examples, electrodes may be positioned downstream of the brushes on either side of the brushes to effect a cathodic cleaning of the surface of the sample to remove loosely adhering soil. Such cathodic cleaning is effected by reversing the polarity of the sample 310, so as to generate from the electrolyte some hydrogen at the sample surface, sufficient to loosen the dirt but no slag or inclusions in the sample.

Figure 9:
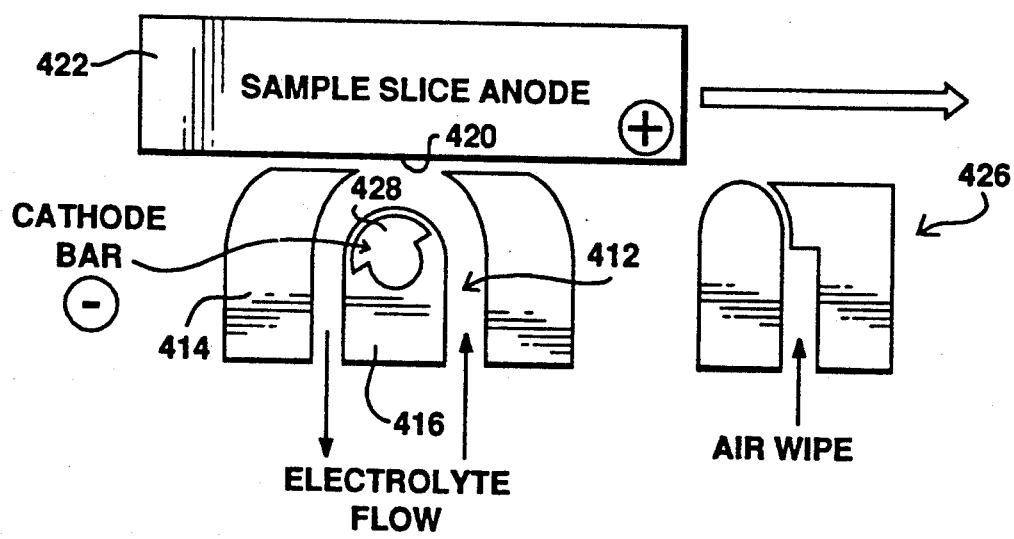
FIG. 9 is a close-up of one alternative form of the etching station used in the apparatus of FIG. 8.

FIG. 9 illustrates a modified form of the acid etch station. As seen therein the electrolyte flow is confined within a flow channel 412 formed in a guide member 414 and divided into inlet and outlet portions by a baffle member 416 which supports a rod-like cathode 418 at the upper extremely thereof. The flow channel 412 has an upper opening 420 opposite the cathode 418.

The sample 422 to be etched passes in close proximity to the opening 420 so as to be contacted by electrolyte flowing through the channel 412 while an electrical current is applied between the anodic sample 422 and the cathode 418 to effect etching of the surface. Before leaving the acid etch station, the sample is air wiped by a jet of air ejected from air wipe mechanism 424.

The embodiment of FIGS. 7 and 8 represents a preferred method and apparatus for the processing of steel slabs. Accordingly, in one preferred aspect of the present invention, there is provided a method of effecting etching of a generally rectangular sample having a smooth surface to be etched to determine the internal quality of a mass of metal from which the sample is removed, which comprises loading the sample in a sample carrier with the smooth surface facing downwardly; transporting the sample in the carrier through a rectilinear path from a loading station successively through an etch station and wash station to an unload station; applying a positive electrical potential tot he sample and a negative electrical potential to an elongate bar extending transverse to the rectilinear path of travel in the etch station while the sample is transported through the etch station; activating a flow of aqueous etchant over the smooth surface to be etched when the sample is in the etch station, whereby a current passes between the bar and the surface to be etched and metal is etched from the surface; activating a flow of cleaning solution over the etched surface of sample when the sample is in the wash station; deactivating the flow of aqueous etchant when the sample exits the etch station; deactivating the flow of cleaning solution and when the sample exits the wash station; and unloading the sample from the sample carrier in the unloading station.

In another preferred aspect of this invention, there is provided an apparatus for effecting etching of a generally rectangular sample having a smooth surface to be etched to determine the internal quality of a mass of metal from which the sample is removed, which comprises sample transport means for receiving the sample and transporting the sample through the apparatus in a rectilinear substantially horizontal path; etch station means comprising an elongate electrode mounted transverse to the rectilinear path and etchant applying means for applying etchant to the smooth surface of the sample when located in the etch station means; electric power means for applying a positive electrical potential to the sample and a negative electrical potential to the elongate electrode to cause current to flow therebetween when etchant is applied to the smooth surface of the sample; wash station means comprising cleaning solution application means for applying a cleaning solution to the etched surface of the sample when located in the wash station means; first position sensing means for activating the etchant applying means when the sample transport means enters the etch station means; and second position sensing means when for activating the cleaning solution application means when the sample transport means enters the wash station means.

EXAMPLES

Example 1

The apparatus of FIGS. 3 and 4 was employed to effect anodic dissolution of steel from samples taken from continuously cast billets, blooms and slabs for the purpose of determining the internal quality of the samples and certain parameters were measured and determined. This data then was tabulated and compared to corresponding typical parameters of the acid etching employed in the rapid acid soluble aluminum determination procedure described in the aforementioned U.S. Pat. No. 4,533,642 using cold dilute acid, that same aluminum determination procedure as carried out with hot acid and the parameters typically employed for the conventional hot acid etch procedure for revealing internal quality.

The results obtained are set forth in the following Table I:

TABLE I

COMPARISON OF HOT ACID AND ELECTROLYSIS FOR STEEL DISSOLUTION

| No. | Parameter | Steel Dissolution by Conventional Hot Acid | | | | Steel Dissolution by Cold Dilute Acid Using Electrolysis | | | |
|---|---|---|---|---|---|---|---|---|---|
| | | Acid Soluble Aluminum Determination | Slab | Bloom | Billet | Acid Soluble Aluminum Determination | Slab | Bloom | Billet |
| 1. | SAMPLE | | | | | | | | |
| | Size before cutting mm | 32 × 38 | 240 × 2032 | 330 × 610 | 100 × 100 | 32 × 38 | 240 × 2032 | 330 × 610 | 100 × 100 |
| | Size after cutting | | | | | | | | |
| | Thickness mm | 6 | 240 × 300 | 330 × 200 | | 6 | 240 × 300 | 330 × 200 | 100 × 100 |
| | Face area cm² | 10 | 50 | 50 | 64 | 10 | 50 | 50 | 64 |
| | Weight kg | .047 | 720 | 660 | 100 | .047 | 720 | 660 | 100 |
| | | | 28 | 26 | 4.99 | | 28 | 26 | 4.99 |
| 2. | TANK CAPACITY | | | | | | | | |
| | Sample size (max) | (0.5 g) Chips | 330 × 330 × 70 | 330 × 330 × 70 | 150 × 150 × 100 | 380 × 6 (round sample) | 330 × 330 × 70 | 330 × 330 × 70 | 150 × 150 × 100 |
| | Tank Size -L | 0.10 | 30 | 30 | 10 | 0.02 | 10 | 10 | 3 |
| | Reservoir Size -L | 10 | | | | 10 | 180 | 180 | 90 |
| 3. | STEEL DISSOLVED | | | | | | | | |
| | Weight - g | 0.5 | 64.82 | 64.82 | 10.42 | .0926 | 32.41 | 32.41 | 5.21 |
| | Thickness - um | (Chips) | 58 × 2 | 63 × 2 | 67 × 2 | 12 | 58 | 63 | 67 |
| 4. | HCl USED PER SAMPLE | | | | | | | | |
| | Weight - HCl - g | 0.65 | 85 | 85 | 13.6 | 0.121 | 42 | 42 | 6.8 |
| 5. | COULOMBS PER SAMPLE (amp × sec) | | | | | 320 (16 × 20) | 112,000 (350 × 320) | 112,000 (350 × 320) | 18,000 (200 × 90) |
| 6. | HYDROGEN PER SAMPLE volume @ ntp - L | 0.20 | 26 | 26 | 4.2 | 0.037 | 13 | 13 | 2.09 |
| 7. | ELAPSED TIME FOR DISSOLUTION approx. sec | 1200 | 1200 | 1300 | 1400 | 20 | 320 | 320 | 90 |
| 8. | MAX. NO. OF SAMPLES PER TANK OF ACID | 100 | 10 | 10 | 11 | 500 | 125 | 125 | 390 |
| 9. | MIN. REQUIRED SUPPLY AIR TO AVOID EXPLOSION - L/min | 0.073 | 27 | 27 | 36 | 2.2 | 50 | 50 | 28 |
| 10. | ACID 'RECIPE' (per tank) | | | | | | | | |
| | Tech. Grade-HCl-L | 5 | 15 | 15 | 5 | .0018 | 27.8 | 27.8 | 13.9 |
| | Makeup Water-L | 5 | 15 | 15 | 5 | .019 | 154. | 154. | 77 |
| 11. | SPEND ACID (per tank) | | | | | | | | |
| | Weight-HCl-g | 212 | 637 | 637 | 212 | .0765 | 1326 | 1326 | 663 |
| | Weight-FeCl₂-g | 3325 | 9974 | 9974 | 3325 | 1.197 | 9216 | 9216 | 4608 |
| | Concentration - | | | | | | | | |
| | HCl-g/L | 42.5 | 42.5 | 42.5 | 42.5 | .00765 | 7.3 | 7.3 | 7.3 |
| | FeCl₂-g/L | 665 | 665 | 665 | 665 | .1197 | 51. | 51. | 51. |
| 12. | ACID RECIRCULATION RATE - L/min | | | | | 0.5 | 23 | 23 | 23 |

TABLE I-continued

COMPARISON OF HOT ACID AND ELECTROLYSIS FOR STEEL DISSOLUTION

| No. | Parameter | Steel Dissolution by Conventional Hot Acid | | | | Steel Dissolution by Cold Dilute Acid Using Electrolysis | | | |
|---|---|---|---|---|---|---|---|---|---|
| | | Acid Soluble Aluminum Determination | Slab | Bloom | Billet | Acid Soluble Aluminum Determination | Slab | Bloom | Billet |
| 13. | EFFECTIVE CURRENT DENSITY - amp/cm² | | | | | 1.60 | 4.66 | 4.17 | 7.87 |
| 14. | INDEX of Item 12/ Item 13 | | | | | 0.31 | 4.93 | 5.52 | 2.92 |
| 15. | TEMPERATURE °C. | 71 to 82 | 71 to 82 | 71 to 82 | 71 to 82 | 10 to 40 | 10 to 40 | 10 to 40 | 10 to 40 |

As may be seen from the above Table I, the procedure of the present invention contrasts markedly with the conventional hot acid etch procedures for internal quality determination and for acid soluble aluminum determination in the process conditions involved. The ability to employ near ambient temperatures eliminates the tendency to fume formation from the etchant.

In addition, the procedure of the present invention contrasts markedly with our electrolytic acid soluble aluminum determination procedure.

The samples treated in the two procedures are of entirely different sizes and the process conditions employed to effect, on the one hand, dissolution of iron and aluminum to determine aluminum content and, on the other hand, dissolution of iron to determine internal quality and results obtained by the two procedures are entirely different.

Example 2

The apparatus illustrated in FIG. 8 was employed to effect anodic dissolution of steel from samples taken from continuously cast slabs for the purpose of determining the internal quality of the samples nd certain parameters were measured. These parameters were tabulated along with the corresponding parameters for the slab samples in Example 1, for comparison.

The results obtained are set forth in the following Table II:

TABLE II

| Parameter | FIG. 8 | Example 1 |
|---|---|---|
| 1. Sample - Slab | 12" × 20" (300 mm × 500 mm) | 9½" × 12" (240 mm × 300 mm) |
| 2. Steel Dissolved - Thickness (um) | 19 | 58 |
| 3. Elasped time for dissolution (sec) | 200 | 320 |
| 4. Scan Rate | | |
| (in/min) | 6 | 2.25 |
| (cm/min) | 15.2 | 5.7 |
| 5. Gap between anode and cathode (cm) | 0.74 | 1.27 |
| 6. Current (amps) | 400 | 350 |
| 7. Acid Recirculation (1) Rate (see unit below) | 2.22 | 0.75 |
| 8. Current density (2) (amps/sq.cm) | 5.2 | 4.66 |
| 9. Index of Item 7/ Item 8 | 0.43 | 0.16 |

Notes:
(1) Circulation is calculated to recognize the "Gap" and its affect on the velocity of the etchant across the face of the sample being etched. Unit of rate expressed as "liters per minute per cm of sample width per cm of gap".
(2) Current density = current per unit area sample adjacent the cathode that is being etched.

Example III

Additional experimentation was effected using the apparatus of FIGS. 7 and 8 for a series of steel samples to establish a relationship of thickness etched to other parameters of the procedure.

The data obtained is set forth in the following Table III:

TABLE III

| | SLAB | BLOOM | BILLET |
|---|---|---|---|
| J (amperes per inch) | 37.0 | 44.5 | 50.8 |
| S (inch per minute) | 2.21 | 2.44 | 2.81 |
| t (thickness etched mls) | 2.28 | 2.48 | 2.45 |
| I/Aeff (amp/cm²) | 7.64 | 9.20 | 10.50 |

As may be seen from the data presented in this Table III, the relationship for steel samples is:

$t = 0.136 \times J/S$

SUMMARY OF DISCLOSURE

In summary of this disclosure, the present invention provides a novel procedure for the determination of the internal quality of steel samples by a rapid room temperature electrolytic etching of the sample using dilute hydrochloric acid or other aqueous etchant. Modifications are possible within the scope of this invention.

What we claim is:

1. A method of determining the internal quality of a mass of metal, which comprises:
   removing a sample from said mass,
   electrolytically etching metal from a surface of said sample using an aqueous etchant for said metal which does not significantly react with the metal in the absence of an electric current to remove at least about 0.5 mil (about 12 μm) of metal from the surface of the sample so as to expose a surface representative of the internal quality of the mass of metal from which the sample was taken,
   treating the etched surface of the sample to remove aqueous etchant and any deposit therefrom and drying the etched surface, and
   visually assessing the etched surface of the sample for its internal quality.

2. The method of claim 1 wherein said mass of metal is in the form of an ingot, slab, bloom, billet, bar, forging, casting and/or welded fabrication.

3. The method of claim 2 wherein said mass of metal is a metal selected from the group consisting of iron, nickel, chromium and any alloy thereof.

4. The method of claim 3 wherein said mass of metal is a steel selected from plain carbon steel, low alloy steel, tool steel and stainless steel.

5. The method of claim 4 wherein about 1 to about 5 mils (about 25 to about 125 μm) of steel are removed from said surface of the sample by electrolytic action.

6. The method of claim 1 wherein said etched surface is treated by washing to remove spent etchant and then, when present, removing a black gelatinous coating formed during said etching procedure.

7. A method of determining the internal quality of a mass of metal, which comprises:
   removing a sample from said mass,
   cold machining a surface of said sample to remove any heat-affected zone and to provide a surface having a peak-to-valley roughness (R$_Z$) of less than about 6.8 μm,
   electrolytically etching metal from a surface of said cold machined sample using an aqueous etchant for said metal which does not significantly react with the metal in the absence of an electric current to remove at least about 0.5 mil (about 12 μm) of metal from the surface of the sample so as to expose a surface representative of the internal quality of the mass of metal from which the sample was taken,
   treating the etched surface of the sample to remove aqueous etchant and any deposit therefrom and drying the etched surface, and
   visually assessing the etched surface of the sample for its internal quality.

8. A method of determining the internal quality of a mass of metal in the form of an ingot, slab, bloom, billet, bar, forging, casting and/or welded fabrication of a steel selected from plain carbon steel, low alloy steel, tool steel and stainless steel, which comprises:

removing a sample from said mass, electrolytically etching metal from a surface of said sample using an aqueous etchant for said metal which does not significantly react with the metal in the absence of an electric current to remove about 1 to about 5 mils (about 25 to about 125 μm) of steel are removed from said surface of the sample by electrolytic action so as to expose a surface representative of the internal quality of the mass of metal from which the sample was taken, wherein said electrolytic etching is carried out using about 100 to about 600 amps of electrical power applied to the sample at an effective current density of about 4 to about 24 amps/cm$^2$, treating the etched surface of the sample to remove aqueous etchant and any deposit therefrom and drying the etched surface, and visually assessing the etched surface of the sample for its internal quality.

9. The method of claim 8 wherein said etched surface is treated by washing to remove spent etchant and then, when present, removing a black gelatinous coating formed during said etching procedure.

10. A method of determining the internal quality of a mass of metal in the form of an ingot, slab, bloom, billet, bar, forging, casting and/or welded fabrication of a steel selected from plain carbon steel, low alloy steel, tool steel and stainless steel, which comprises:

removing a sample from said mass, electrolytically etching metal from a surface of said sample using an aqueous etchant for said metal which does not significantly react with the metal in the absence of an electric current to remove about 1 to about 5 mils (about 25 to about 125 μm) of steel are removed from said surface of the sample by electrolytic action so as to expose a surface representative of the internal quality of the mass of metal from which the sample was taken, by relative movement of said sample as an anode with respect to a cathode, wherein thickness of metal etched from the sample is determined by the relationship:

$$t = 0.136 \times J/S$$

where t is the thickness of metal removed, J is the amperes per inch width of sample and S is the scan rate of relative movement of anode and cathode in inches per minute, treating the etched surface of the sample to remove aqueous etchant and any deposit therefrom and drying the etched surface, and visually assessing the etched surface of the sample for its internal quality.

11. The method of claim 10 wherein the current applied between said anode and cathode is about 33 to about 50 amperes per unit of sample width.

12. A method of determining the internal quality of a mass of metal in the form of an ingot, slab, bloom, billet, bar, forging, casting and/or welded fabrication of a steel selected from plain carbon steel, low alloy steel, tool steel and stainless steel, which comprises:

removing a sample from said mass, electrolytically etching metal from a surface of said sample using an aqueous etchant for said metal which does not significantly react with the metal in the absence of an electric current to remove about 1 to about 5 mils (about 25 to about 125 μm) of steel are removed from said surface of the sample by electrolytic action so as to expose a surface representative of the internal quality of the mass of metal from which the sample was taken, wherein said electrolytic etching is effected using dilute hydrochloric acid having an acid normality of about 0.1 to about 3.0 N and at a temperature of about 10° to about 40° C., treating the etched surface of the sample to remove aqueous etchant and any deposit therefrom and drying the etched surface, and visually assessing the etched surface of the sample for its internal quality.

13. The method of claim 12 wherein said dilute hydrochloric acid has an acid normality of about 0.2 to about 2.0 N and the electrolytic etching is effected at a temperature of about 20° to about 30° C.

14. The method of claim 12 wherein said electrolytic etching is effected for about 40 to about 400 seconds.

15. The method of claim 14 wherein said sample is provided as said anode and is spaced from a cathode for said electrolytic etching, hydrogen produced at the cathode during said etching is displaced from between the anode and cathode and reaction products formed during said etching are rapidly moved away from the surface of said sample.

16. The method of claim 15 wherein said hydrogen displacement and removal of reaction products is effected by recirculating said aqueous etchant between said anode and cathode at a recirculation rate of etchant of about 1.6 to about 3.2 L/min/cm of sample width/cm of gap.

17. The method of claim 16 wherein said sample is a billet sample, said cathode is in the form of a plate situated parallel to said sample, said anode and cathode are maintained stationary relative to one another during said electrolytic etching, said cathode is perforated and electrolyte is circulated between said anode and cathode and through the perforated cathode to effect said hydrogen displacement and said reaction products removal.

18. The method of claim 16 wherein said cathode is in the form of an elongate circular bar extending transversely of the sample, and relative movement is effected between said anodic sample and said elongate circular bar cathode during said electrolytic etching such that the elongate circular bar traverse the whole of the surface to be etched while spaced a uniform distance from the anodic sample.

19. The method of claim 18 wherein electrolyte directing means is provided associated with said cathode for directing electrolyte onto the surface of said sample while an electric current is applied between the cathode and anode to effect said electrolytic dissolution, said hydrogen displacement and said reaction products removal.

20. The method of claim 19 wherein said sample is a slab sample or bloom sample and is immersed in a bath of electrolyte while said relative movement is effected.

21. The method of claim 16 wherein said etched surface is treated by washing to remove spent etchant and then, when present, removing a black gelantinous coating formed during said etching procedure.

22. The method of claims 6, 9 or 21 wherein said removal of said black gelatinous coating is effected by scrubbing the surface and effecting cathodic cleaning of the sample surface.

23. The method of claims 1, 8 or 16 wherein, following said etching step, said etched surface is subjected to an alkaline rinse to neutralize trapped acid sites in the surface, so as to form darkly-colored hydrated iron oxide which can be readily observed visually, facilitating identification of the internal quality of the steel sample.

24. The method of claim 15 wherein said cathode is in plate-like form and is located in fixed relation to said sample, an insulating plate having an elongate slot therein is positioned between said anode and cathode, and relative movement is effected between said insulating plate and said sample during said electrolytic etching such that the elongate slot traverses the whole of the surface to be etched while spaced a uniform distance from the anodic sample.

* * * * *